US008821904B2

(12) United States Patent (10) Patent No.: US 8,821,904 B2
Di Pietro (45) Date of Patent: Sep. 2, 2014

(54) TOPICAL COMPOSITION AND USE THEREOF FOR THE PROPHYLAXIS AND THE TREATMENT OF DEFECTS CONNECTED TO INFLAMMATORY DERMOPATHIES

(75) Inventor: Antonino Di Pietro, Gorgonzola (IT)

(73) Assignee: Skinius S.R.L., Gorgonzola (MI) (IT)

( * ) Notice: Subject to any disclaimer, the term of this patent is extended or adjusted under 35 U.S.C. 154(b) by 0 days.

(21) Appl. No.: 13/696,070

(22) PCT Filed: May 4, 2011

(86) PCT No.: PCT/EP2011/057128
§ 371 (c)(1),
(2), (4) Date: Jan. 3, 2013

(87) PCT Pub. No.: WO2011/138364
PCT Pub. Date: Nov. 10, 2011

(65) Prior Publication Data
US 2013/0101686 A1 Apr. 25, 2013

(30) Foreign Application Priority Data
May 6, 2010 (EP) .................................. 10162178

(51) Int. Cl.
| A61K 8/02 | (2006.01) |
| A61K 8/37 | (2006.01) |
| A61K 8/67 | (2006.01) |
| A61K 31/215 | (2006.01) |
| A61K 9/00 | (2006.01) |
| A61K 33/06 | (2006.01) |
| A61K 31/232 | (2006.01) |
| A61K 8/60 | (2006.01) |
| A61K 9/06 | (2006.01) |
| A61K 45/06 | (2006.01) |
| A61K 8/26 | (2006.01) |
| A61Q 19/00 | (2006.01) |
| A61Q 19/08 | (2006.01) |
| A61K 31/07 | (2006.01) |
| A61K 31/192 | (2006.01) |

(52) U.S. Cl.
CPC .............. *A61K 33/06* (2013.01); *A61K 8/375* (2013.01); *A61K 8/671* (2013.01); *A61K 31/215* (2013.01); *A61K 9/0014* (2013.01); *A61K 31/232* (2013.01); *A61K 8/602* (2013.01); *A61K 9/06* (2013.01); *A61K 45/06* (2013.01); *A61K 8/26* (2013.01); *A61Q 19/008* (2013.01); *A61Q 19/00* (2013.01); *A61Q 19/08* (2013.01); *A61K 31/07* (2013.01); *A61K 31/192* (2013.01)
USPC ............. 424/401; 424/698; 514/99; 514/725

(58) Field of Classification Search
USPC .............................. 424/401, 698; 514/99, 725
See application file for complete search history.

(56) References Cited

U.S. PATENT DOCUMENTS

| 5,523,090 A | 6/1996 | Znaiden et al. |
| 5,560,917 A | 10/1996 | Cohen et al. |
| 5,723,139 A | 3/1998 | Granger et al. |
| 2011/0027221 A1* | 2/2011 | Fu et al. ....................... 424/85.2 |

FOREIGN PATENT DOCUMENTS

| JP | 2004123675 A | * | 4/2004 |
| WO | 2005067946 | | 7/2005 |
| WO | WO-2009-038444 A1 | * | 3/2009 |

OTHER PUBLICATIONS

Sampaio Alb et al., "Seborrheic dermatitis", An. Bras. Dermatol., 2011, vol. 86, No. 6:1061-71.
Del Rosso JQ, "Adult Seborrheic Dermatitis: A Status Report on Practical Topical Management", J Clin Aesthet Dermatol., May 2011; 4(5):32-8.
Peyrí J et al., and the Spanish Group of the Sebderm Study, "Clinical and Therapeutic Profile and Quality of Life of Patients With Seborrheic Dermatitis", Actas Dermosifiliogr, 2007;98:476-82.
Harding CR et al., "Dandruff: a condition characterized by decreased levels of intercellular lipids in scalp stratum corneum and impaired barrier function", Arch Dermatol Res., 2002;294(5):221-30. (only abstract).
Passi S et al., "Blood levels of vitamin E, polyunsaturated fatty acids of phospholipids, lipoperoxides and glutathione peroxidase in patients affected with seborrheic dermatitis", J Dermatol Sci,May 1991; 2(3) :171-8. (only abstract).
Burton JL et al., "Seborrhoea is not a feature of seborrhoeic dermatitis", Br Med J (Clin Res Ed), Apr. 9, 1983;286 (6372):1169-70. (only abstract).
Dawson TL Jr., Malassezia globosa and restricta: breakthrough understanding of the etiology and treatment of dandruff and seborrheic dermatitis through whole-genome analysis', J Investig Dermatol Symp Proc., Dec. 2007;12 (2):15-9. (only abstract).
Kim MY et al., "Retinoid Induces the Degradation of Corneodesmosomes and Downregulation of Corneodesmosomal Cadherins: Implications on the Mechanism of Retinoid-induced Desquamation", Ann Dermatol, Nov. 2011 ;23(4): 439-47. (only abstract).

(Continued)

*Primary Examiner* — Ali Soroush
(74) *Attorney, Agent, or Firm* — Novak Druce Connolly Bove + Quigg LLP

(57) ABSTRACT

A topical composition and its use for the prophylaxis and the treatment of defects connected to inflammatory dermopathies. Particularly, a topical composition including at least an alum, 18-β-glycyrrhetic acid and/or one derivative thereof, and vitamin A and/or one derivative thereof, and the use of such composition for the prophylaxis and the treatment of inflammatory dermopathies, preferably of the seborrhoeic dermatitis and of those affections in which the presence of an excess of sebum occurs.

23 Claims, No Drawings

(56) References Cited

OTHER PUBLICATIONS

Schwartz R. A. et al., "Seborrheic Dermatitis: An Overview", Am Fam Physician. Jul. 1, 2006;74(1):125-132. (only abstract).

Fiore C et al., "A history of the therapeutic use of liquorice in Europe", J Ethnopharmacol., Jul. 14, 2005;99(3):317-24. (only abstract).

Harding CR et al., "Dandruff: a condition characterized by decreased levels of intercellular lipids in scalp stratum corneum and impaired barrier function", Arch Dermatol Res., 2002;294(5):221-30.

Passi S et al., "Blood levels of vitamin E, polyunsaturated fatty acids of phospholipids, lipoperoxides and glutathione peroxidase in patients affected with seborrheic dermatitis", J Dermatol Sci,May 1991; 2(3) :171-8.

Burton JL et al., "Seborrhoea is not a feature of seborrhoeic dermatitis", Br Med J (Clin Res Ed), Apr. 9, 1983;286 (6372):1169-70.

Dawson TL Jr., Malassezia globosa and restricta: breakthrough understanding of the etiology and treatment of dandruff and seborrheic dermatitis through whole-genome analysis', J Investig Dermatol Symp Proc., Dec. 2007;12 (2):15-9.

Kim MY et al., "Retinoid Induces the Degradation of Corneodesmosomes and Downregulation of Corneodesmosomal Cadherins: Implications on the Mechanism of Retinoid-induced Desquamation", Ann Dermatol, Nov. 2011 ;23(4): 439-47.

Fiore C et al., "A history of the therapeutic use of liquorice in Europe", J Ethnopharmacol., Jul. 14, 2005;99(3):317-24.

Wrinkles, Wikipedia, URL: < http://en.wikipedia.org/wiki/Wrinkles >, retrieved from the Internet Feb. 25, 2014.

Di Pietro, A., "A Compound Containing Aluminium Potassium Bisulphite, 18[beta]-glycirretic acid and retinyl palmitate (Alukina(R)) in the Treatment of Seborrheic Dermatitis", Journal of Plastic Dermatology, vol. 6, No. 1, Jun. 14, 2010, 33-35 (w/Abstract).

\* cited by examiner

TOPICAL COMPOSITION AND USE THEREOF FOR THE PROPHYLAXIS AND THE TREATMENT OF DEFECTS CONNECTED TO INFLAMMATORY DERMOPATHIES

CROSS-REFERENCE TO RELATED APPLICATIONS

This application is a §371 National Stage Application of International Application No. PCT/EP2011/057128, filed on 4 May 17 2011, claiming the benefit of European Patent Application No. 10162178.7 filed on 6 May 2010.

The present invention refers to a topical composition and to its use for the prophylaxis and the treatment of defects connected to inflammatory dermopathies. Particularly, the invention pertains to a topical composition comprising at least an alum, 18-β-glycyrrhetic acid and/or one derivative thereof, and vitamin A and/or one derivative thereof, and the use of such composition for the prophylaxis and the treatment of inflammatory dermopathies, preferably of the seborrhoeic dermatitis and of those affections in which the presence of an excess of sebum occurs.

Dermatitis is an expression of an inflammatory, immune reaction of the skin, and manifests itself under the form of irritation. Particularly, the seborrhoeic dermatitis is an inflammatory form, acute of dermatitis, often chronic, that—generally-interests subjects having fat skin, in the body areas rich in sebaceous glands such as the scalp, the face, the trunk and that can be located in the areas of the folds, i.e. rather the armpit, the undermammary curl, the navel and the groin, characterized by the formation of oily, humid or dry, flakes, and from the formation of yellowish spots that originate crusts and cause strong itches.

Statistically, the seborrhoeic dermatitis has a percentage incidence on the population, having a preference for the males to the females, approximately of the 1-3%; such percentage slightly raises to 3-5%, exclusively considering the bracket between 15 and 45 years.

In the last years, the seborrhoeic dermatitis has reawakened the attention of the physicians because of its frequent appearance in the patients affected by acquired immune deficiency syndrome (AIDS), among which a 30% incidence occurs in case of HIV+ seropositivity and of the 83% in case of ascertained AIDS.

The therapies till now used for resolving such pathologies have mainly used topical corticosteroids such as betametasone valeriate, diflucortolone valerianate and hydrocortisone butirrate.

The cortisone ointments involve nevertheless a weakening of the cutaneous defences that induces a cutaneous thinning; another drawback, consists in the appearance of hypertrichosis and teleangectasias, aesthetically undesirable, especially for women. Besides, the continuous use of such medicines brings about to addiction and consequently to a progressive increase of dosage.

Other therapies use antimycotic medicines, topically applied, among which particularly ketoconazole. The application brings to an improvement of seborrhoeic eczema in 75% of the cases after four weeks of treatment (C. A. Green, P. M. Farr, S. Shuster "Treatment of Seborrhoeic Dermatitis of the face, scalp and trunk to topical ketoconazole" Br. J. Dermatol. 116, p. 217-221, 1986); the response to the medicine is therefore rather slow and not necessarily decisive of the pathology.

It is opportune to notice as, besides the obvious pathological complications, the establishing on the skin of a seborrhoeic dermatitis brings to evident aesthetical decompensations that produces negative psychological effects on the patient, deteriorating his social relationships and carrying to, in the extreme cases, in anxious-depressive syndromes.

Alums are inorganic salts used in cosmetics because of their strong astringent and haemostatic activities, particularly in the products for the trimming (after shave, haemostatic, etc.) and in axillary and palm-plantar hyperhidroses and they are also used in colluttoria, because of weak antiseptic properties.

The 18-β-glycyrrhetic acid or enoxolone [(3β,20β)-3-hydroxy-11-oxoolean-12-en-29-oic acid, CAS Registry Number: 471-53-4, $C_{30}H_{46}O_4$], also known as 18-β-glycirrhetinic acid, is a vegetable product, extracted by hydrolysis from the plant *Glycyrrhiza glabra* (liquorice), having an anti-inflammatory and anti-viral action, of renown cosmetic use, particularly due to the action of protection of capillary vessels. Besides, it shows cytoprotective and emollient, decongestant and riepithelizing activities, coadjutant in the treatment of the wrinkles and the cutaneous strias, and it also contributes to the reduction of cutaneous flushes.

Glycyrrhizin (synonyms: glycyrrhizic acid and glycyrrhizinic acid), one of the main components of *Glycyrrhiza glabra* (liquorice), is a glucoside triterpene wherein the triterpene structure consists in glycyrrhetinic acid, to which two residues of iduronico acid are linked. Glucuronic and glycyrrhetic acids are obtained by hydrolysis from glycyrrhizin.

Vitamin A is a liposolubile vitamin that exists in nature substantially in three forms: alcoholic (retinol), aldehydic (retinaldehyde) and acid (retinoic acid) forms. In the present specification, by "vitamin A" are meant both such forms and their analogues and precursors. For example, retinoids, analogues of retinol, of which around 1500, natural and synthetic, types are known, are therefore comprised, together with carotenoids, precursors of retinol, showing the biological activity of vitamin A, since they can act as provitamins, able to evolve, through metabolic enzymes, in the biologically active form.

It is known how vitamin A and, particularly, retinil palmitate, one of the derivatives of retinol most widely used, for instance, as softener and restitutive, in cosmetics, contributing to cellular renovation, accelerate the removal of dead cells from the horny layer and, consequently reduce the cutaneous defects.

The purpose of the present invention is that to find a formulation effective in the prophylaxis and in the treatment of defects connected to inflammatory dermopathies, particularly of seborrhoeic dermatitis and in those affections in which the presence of an excess of sebum occurs, that shows—at the same time—a significant reduction of the consequential anti-aesthetic effects deriving from the pathology.

Another purpose of the present invention consists in obtaining a rapid remission, in total absence of collateral effects, also with high dosages.

It has been now found that a composition comprising at least an alum, 18-β-glycyrrhetic acid and/or one derivative thereof, and vitamin A and/or one derivative thereof, independently from the activities known for each compound, shows an unexpected effectiveness in the prophylaxis and the treatment of inflammatory dermopathies, especially of the cutaneous defects linked thereto, preferably in the presence of seborrhoeic dermatitis and of those affections in which an excess of sebum occurs.

According to a first aspect, the invention concerns to a topical composition comprising:

a) at least an alum selected among the group constituted by aluminium and an alkaline metal or ammonium double sulfates;

b) 18-β-glycyrrhetic acid and/or one salt and/or organic or inorganic derivative thereof;

c) vitamin A and/or one derivative thereof; and d) at least a vehicle or an excipient cosmetically acceptable.

Particularly, the composition of the present invention includes:

a) 0.1-97.0%, preferably 0.3-80.0% and, particularly 0.5-60.0% by weight of at least an alum;

b) 0.1-1.0%, preferably 0.2-0.8% and, particularly 0.3-0.6% by weight of 18-(3-glycyrrhetic acid and/or one salt and/or organic or inorganic derivative thereof;

c) 0.1-1.0%, preferably 0.2-0.8% and, particularly 0.3-0.6% by weight of vitamin A and/or one derivative thereof, simple and/or hydrogenated and/or a retinoic acid ester or derivatives thereof and/or mixtures obtained by reacting retinol and saccharomycetes polypeptides; and d) at least a vehicle or an excipient cosmetically acceptable.

In the present description, the term "alum" means a compound selected among aluminium and an alkaline metal or ammonium double sulfates, in all the crystalline forms thereof, the hydrated forms thereof comprised too, wherein water molecules can also enter the crystalline network and whose number varies from 1 to 20. Among these alums, potassium undecahydrate or dodecahydrate are preferred.

Besides 18-β-glycyrrhetic acid, salts and organic or inorganic derivatives thereof are preferred, selected among the 18-β-glycyrrhetic acid derivatives named in the European inventory of cosmetic ingredients (see, for example the web page: http://ec.europa.eu/enterprise/sectors/cosmetics/cosing/ingredients/index_en.htm) and, in particular, from the group consisting of ammonium 18-β-glicyrrhyzate (CAS 53956-04-0), potassium (CAS 68039-19-0) and dipotassium (CAS 68797-35-3) 18-β-glicyrrhyzzate, disodium (CAS 71277-79-7) and trisodium (CAS 71277-78-6) 18-β-glicyrrhyzzate, methyl 18-β-glicyrrhyzzate (CAS 104191-95-9) and hydrolyzed 18-β-glycyrrhizzate (CAS 222400-67-1).

As to vitamin A, besides to simple and/or hydrogenated retinol (CAS 68-26-8), the vitamin A derivatives selected from the group consisting of retinoic acid esters such as, for instance retinil palmitate (CAS 79-81-2), retinil linoleate (CAS 631-89-0) and retinoxytrimethylsilane (CAS 16729-19-4) and/or mixtures obtained by reacting retinol and saccharomycetes polypeptides, are preferred.

Examples of cosmetically acceptable excipients or vehicles for the compositions of the invention are diluents, for example lactose, dextrose, saccharose, cellulose, lubricating agents, for example silica, talc, stearic acid, vaseline oil, natural and synthetic hydrocarbons, glyceride and non-glyceride esters, fatty alcohols, cyclic and linear, silicone derivatives, synthetic and natural waxes, paraffins, fatty acids, magnesium or calcium stearate, glycerine, sorbitol, maltitol, monopropilenico glycol, polyethylene glycols; binding agents, for example starches, arabic rubbers, gelatin, methylcellulose, carboxymethylcellulose or polyvinylpyrrolidone; dyes; anionic emulsifying agents such as all stearates, non-ionic ones such as saccharose esters, glucose esters, ethoxylated fatty alcohols, glyceryl monostearates, anionic surfactants as sodium lauryl ethoxy sulfate, sodium lauryl ethoxy citrate, non-ionic ones such as glucose esters, amphoteric sorbitol esters such as cocoamidopropylbetaine, cocoimidazoline, preservative agents such as hydroacetates and dehydroacetates, organic aliphatic and aromatic esters, polymers, imidazolidinyl urea, p-oxybenzoates, methylisothiazolinone and methylisothiazolinone chloride, sorbico acid; seizing agents as ethylene diaminotetracetic acid, sweeteners; extracts and vegetable derivatives, particularly isoflavones, phytosterols and soy lecithin, inorganic salts, vitamins different from vitamin A and esters thereof, and generally non-toxic and cosmetically and pharmacologically inactive substances, commonly used in pharmaceutical and cosmetic formulations also in combination with anti-inflammatory, antimycotic and antimicrobial agents.

According to another aspect, the invention concerns the use of the compositions of the invention, according to what above defined, for the treatment and the prophylaxis of inflammatory dermopathies, particularly of the seborrhoeic dermatitis and of the cutaneous defects which derive therefrom, as well as in those affections in which the presence of an excess of sebum occurs, such as, for example, seborrhoea, acne, folliculitis, etc., and/or as coadjutant in contact dermatitis, in eczemas and in psoriasis.

It has been observed that the composition according to the present invention does not involve a weakening of the cutaneous defences; indeed, it has not been observed any thinning of the skin.

Besides, hypertrichosis and teleangiectasies phenomena have not been observed, and, thanks to the effectiveness of the composition of the present invention, it is possible to use low dosages, also avoiding accordingly the risk of possible addictions.

Nevertheless, also the most elevated (and more frequent) dosages typical of a cosmetic treatment do not involve risks for the skin, due to the elevated tolerability of the materials used.

The effectiveness of the treatment with the composition of the present invention resulted equal to 90% of the cases already after the first application; continuing the administration, a practically complete remission has been obtained.

The compositions according to the present invention can be applied in amounts that will vary according to the clinical conditions of the patient to be treated, to the weight and of the age and of the form of the realization used such as, for instance, solutions, suspensions, dispersions, ointments, gel, creams, lotions, wettable dusts.

The compositions of the invention can be prepared using techniques known in the field such as, for instance, mixing and granulating. Besides, since in cosmetics the sensation that the consumer feels during the spreading of the product on the skin is of an extreme importance, it is preferable to pay a particular attention to the formulation of the cosmetic "matrix", so to confer to the composition of the invention, a particular texture.

According to the knowledge of the skilled in the art, the methods of preparation may vary depending on the plant used and of the geometry of the mixer used.

Generally, there are used mixers under vacuum, endowed with turbine; the mixer has normally enslaved from another fusing mixer, the latter also being able to work under vacuum and used in presence of solid components. In the case of the preparation of creams, according to what it results evident for the skilled in the art, the external phase can be either aqueous (O/W) or lipidic (W/O), depending on the emulsifiers used.

It has been noticed how the use of the compositions according to the invention entails an increase of the activities known for the single components, such to show a rapid remission of the pathology (till one week of treatment only) and, contemporarily, an evident reduction, if not disappearance, of the defects to the correlated treated dermopathy. Such synergic effect has also been verified by clinical testing.

The following examples illustrate the invention without limiting it.

COMPOSITION EXAMPLES

All the concentrations shown in the following are expressed as % weight. Besides, the viscosity parameter measured with a Brookfield instrument at 20° C. on the product per se, has to be considered, depending on the range:

low, if lower than 10,000 mPas;
middle, if comprised between 10,000 and 50,000 mPas;
high, if higher than 50,000 mPas.

pH (if measurable) is normally meant with a tolerance of +/−0.3 unities.

Preparation of the Compositions

The formulations of the gel (Composition Example 1), of the detergent (Composition Example 2) and of the solution (Composition Example 3) have been prepared dispersing the alum at first and subsequently mixing the ingredients in a mixer endowed with a turbine and under vacuum, to a temperature between 30 and 35° C.

In the case of the emulsions or of the creams (Examples 4-7), the water phase (comprising the alum, the salts and the inorganic and/or hydrosoluble compounds) and the lipidic phase (comprising the solvents and the organic and/or liposoluble compounds) have been prepared separately, adding perfumes and preservatives only after the preparation of the emulsion resulting from mixing said aqueous and lipidic phases. The two phases are been mixed under vacuum at a temperature equal to 70° C., under stirring for about 10 minutes, and added with preservatives and perfumes only after having brought the temperature below around 40° C.

Example of Composition 1

| Gel-pH 4,5-low viscosity | |
|---|---|
| Distilled water | to 100 |
| Imidazolidinyl urea | 0.30 |
| Disodium EDTA | 0.10 |
| Glycerine | 3.00 |
| 18-β-glycyrrhetic acid | 0.80 |
| Retinil Palmitate | 0.30 |
| p-methyl hydroxy benzoate | 0.15 |
| Phenoxy ethanol | 0.50 |
| Castor oil (40) DE | 2.00 |
| $KAl(SO_4)_2 \cdot 12\, H_2O$ | 3.00 |
| Hydroxyethyl cellulose | 0.50 |

Example of Composition 2

| Detergent-pH 6.5-low viscosity | |
|---|---|
| Sodium lauryl ethoxy sulfate 30% | 12.0 |
| Monoethanolamine lauryl ethoxy sulfate 30% | 18.0 |
| Cocodiethanolamide | 4.0 |
| 18-β-glycyrrhetic acid | 0.3 |
| Retinil Palmitate | 0.3 |
| Perfume | 0.2 |
| Purified water | to 100 |
| Imidazolidinyl urea | 0.3 |
| EDTA | 0.1 |
| Sodium chloride | 1.0 |
| Poliquaternium 10 | 0.2 |
| Triethanolamine 99% | 1.0 |
| Hydrolysed wheat protein | 0.5 |
| $KAl(SO_4)_2 \cdot 12H_2O$ | 3.0 |

Example of Composition 3

| Solution-pH 3.9 | |
|---|---|
| Purified water | to 100 |
| Imidazolidinyl urea | 0.3 |
| 18-β-glycyrrhetic acid | 0.8 |
| Retinil Palmitate | 0.5 |
| Disodium EDTA | 0.1 |
| $KAl(SO_4)_2 \cdot 12H_2O$ | 3.0 |

Example of Composition 4

| Emulsion-pH 4.7-medium viscosity | |
|---|---|
| Purified water | to 100 |
| PEG 8 $C_{12}$-$C_{14}$ alkyl ester | 10.00 |
| $C_{12}$-$C_{15}$ alkyl benzoate | 7.00 |
| Cetyl stearyl alcohol | 2.00 |
| Glycerine | 3.00 |
| Dimeticone | 2.00 |
| Cyclomethicone | 1.00 |
| 18-β-glycyrrhetic acid | 0.50 |
| Retinyl Palmitate | 0.50 |
| Hydrogenated lecithin | 0.50 |
| Imidazolidinyl urea | 0.30 |
| P-methyl hydroxybenzoate | 0.15 |
| P-propyl hydroxybenzoate | 0.15 |
| Disodium EDTA | 0.10 |
| Vitamin and acetate | 0.10 |
| $KAl(SO_4)_2 \cdot 12H_2O$ | 5.00 |

Example of Composition 5

| Cream-high viscosity | |
|---|---|
| Vaseline oil | 16.00 |
| Polyglyceryl 3-diisostearate | 3.70 |
| *Ribes nigrum* (Black currant) fruit extract | 0.50 |
| Polyethylene glycol dipolyhydroxystearate | 0.70 |
| Tocopheryl acetate | 0.20 |
| Retinil palmitate | 0.20 |
| Aperoxid ™ TLA (Biochim) | 0.30 |
| (Mixture of lecithin, tocopherol, ascorbil palmitate and citric acid) | |
| Cyclopentasiloxane | 4.00 |
| Perfume | 0.50 |
| NaCl | 0.40 |
| $MgSO_4$ | 0.40 |
| Phenonip ™ (Formenti) | 0.70 |
| (Mixture of p-hydroxy benzoates, phenoxyethanol) | |
| Glycyrrhizate ammonium | 0.05 |
| $KAl(SO_4)_2 \cdot 12H_2O$ | 10.00 |
| Glycerine | 5.00 |
| 18-β-glycyrrhetic acid | 0.20 |
| Polymethylmetacrilate | 1.00 |
| Water | to 100 |

Example of Composition 6

| Cream-high viscosity | |
|---|---|
| Cetyl stearyl alcohol | 5.600% |
| Lauryl alcohol | 1.000% |
| Aperoxid ™ TLA (Biochim) | 0.030% |

-continued

| Cream-high viscosity | |
|---|---|
| (Mixture of lecithin, tocopherol, ascorbil palmitate and citric acid) | |
| $C_{12}$-$C_{15}$ alkyl benzoate | 1.000% |
| 18-β-glycyrrhetic acid | 0.500% |
| Perfume | 0.150% |
| Phenonip ™ (Formenti) | 0.70 |
| (Mixture of p-hydroxy benzoates, phenoxyethanol) | |
| Quafin ™ CT (Henkel) | 6.300% |
| Retinil palmitate | 0.200% |
| $KAl(SO_4)_2 \cdot 12H_2O$ | 10.00 |
| Imidazolidinyl urea | 0.250% |
| Water | to 100% |

Example of Composition 7

| Cream-high viscosity | |
|---|---|
| Paraffinum liquidum | 16.000 |
| $KAl(SO_4)_2 \cdot 12H_2O$ | 10.000 |
| Glycerine | 5.000 |
| Cyclopentasiloxane | 4.000 |
| Polyglyceril-3 diisostearate | 4.000 |
| Polymethylmetacrilate | 1.000 |
| Phenoxyethanol | 0.700 |
| Perfume | 0.500 |
| NaCl | 0.400 |
| $MgSO_4$ | 0.400 |
| $C_{12}$-$C_{15}$-alkyl benzoate | 0.350 |
| PEG-30 polyhydroxystearate | 0.350 |
| Tocopheryl acetate | 0.200 |
| p-methyl ethylhydroxybenzoate | 0.150 |
| Retinil palmitate | 0.150 |
| 18-β-glycyrrhetic acid | 0.200 |
| Oil of *Helianthus annuus* seeds | 0.090 |
| p-butyl hydroxybenzoate | 0.080 |
| Ammonium glycyrrhizate | 0.050 |
| p-ethyl hydroxybenzoate | 0.050 |
| *Ribes nigrum* (Black currant) fruit extract | 0.050 |
| p-propyl hydroxybenzoate | 0.030 |
| Lecithin | 0.020 |
| Tocopherol | 0.005 |
| Ascorbil palmitate | 0.003 |
| Citric acid | 0.002 |
| Water | to 100 |

Examples 8-10 (effectiveness researches)

A study with three groups of different patients has been carried out to the purpose of testing the in vivo effectiveness of the compositions according to the present invention.

Example 8

Fifty patients, 40 males and 10 females, between 25 and 60 years old, suffering from facial seborrhoeic dermatitis, have been treated with the cream prepared in the composition example No. 7.

All the patients under test were not subjected to other therapies for the seborrhoeic dermatitis since at least fifteen days. Around the 50% of the patients was affected since over one year from the pathology and another about 30% had been suffering since less than one year, only 20% was at its first episode. In conclusion, around 80% of the subjects cured themselves since at least one year without success, with numerous recurrences. The clinical picture of the various patients is reassumed in Table 1.

TABLE 1

| | | | THE SEBORROHEIC DERMATITIS IS PRESENT: | | |
|---|---|---|---|---|---|
| PATIENT | SEX | AGE (YEARS) | AT THE FIRST EPISODE | FROM LESS THAN ONE YEAR | FROM MORE THAN ONE |
| AR | M | 32 | X | | |
| AL | F | 40 | | X | |
| BO | M | 60 | | | X |
| BM | M | 30 | | X | |
| BT | M | 45 | | X | |
| BS | M | 48 | | | X |
| BA | M | 35 | | X | |
| CA | F | 29 | X | | |
| CC | M | 44 | | X | |
| CT | M | 46 | | | X |
| CW | M | 36 | | X | |
| DS | M | 52 | | | X |
| DB | M | 41 | | X | |
| EW | M | 55 | | X | |
| FC | F | 39 | | | X |
| FO | M | 40 | X | | |
| FA | M | 27 | | X | |
| GI | F | 46 | | | X |
| GS | M | 33 | | X | |
| GO | M | 51 | | | X |
| GP | M | 35 | X | | |
| GM | F | 52 | | X | |
| IL | M | 48 | | X | |
| LM | M | 37 | | | X |
| LO | M | 34 | | X | |
| MI | M | 39 | | | X |
| ML | M | 43 | X | | |
| MS | M | 52 | | | X |
| MP | M | 34 | | X | |
| MR | F | 58 | | X | |
| NT | F | 50 | | X | |
| NA | M | 28 | X | | |
| OS | M | 40 | | | X |
| PA | F | 39 | | X | |
| PT | M | 33 | | | X |
| PL | M | 30 | X | | |
| PM | M | 49 | | | X |
| PS | M | 53 | | X | |
| RT | F | 41 | | X | |
| RM | M | 31 | | X | |
| RA | M | 36 | | | X |
| RB | M | 34 | | | X |
| RR | M | 44 | | X | |
| SA | M | 43 | | | X |
| TR | F | 25 | X | | |
| TM | M | 43 | | X | |
| VI | M | 40 | | | X |
| VS | M | 49 | | X | |
| ZA | M | 32 | | X | |
| ZC | M | 29 | | | X |

The application of the cream has been carried out twice a day for 14 consecutive days. At the beginning, the half and the end of the therapeutic cycle, the erythema and the desquamation have been evaluated, according to a scale of values from 0 to 3, as it results from the following Table 2.

TABLE 2

| ERYTHEMA AND DESQUAMATION | BEFORE THE THERAPY | AFTER 7 DAYS | AFTER 14 DAYS | 1 MONTH AFTER THE THERAPY SUSPENSION |
|---|---|---|---|---|
| (3) Intense | 30 patients | 3 patients | 0 patients | 0 patients |
| (2) Middle | 14 patients | 16 patients | 5 patients | 3 patients |
| (1) Light | 6 patients | 21 patients | 8 patients | 12 patients |
| (0) Absent | 0 patients | 10 patients | 37 patients | 35 patients |

The suspension of the application of the cream has been recommended to the patients on the onset of possible side effects which, nevertheless, did not show.

As it results from the Table 2, a net improvement has been obtained in 45 cases, in 5 cases, a good modification of the initial picture has been noted. In the greatest part of the cases, a complete remission has been observed, already after the first application. After one month from the suspension of the therapy, around the 100% of the patients, whom improved at the end of the 14 days of therapy, maintained the result; two patients even improved the clinical picture.

In conclusion, the cream based on of the composition according to the present invention has shown to possess notable therapeutic effectiveness towards seborrhoeic dermatitis. Neither thinning of the skin nor hypertrichosis nor teleangectasias have been observed.

Example 9

One hundred patients, 60 males and 40 females, between 15 and 55 years old, suffering from facial seborrhoeic dermatitis, have been treated with the gel prepared in the composition example No. 1.

The gel has been applied once a day for 14 consecutive days.

At the beginning, the half and the end of the therapeutic cycle, the erythema and the desquamation have been evaluated, according to a scale of values from 0 to 3, as it results from the following Table 3.

TABLE 3

| ERYTHEMA AND DESQUAMATION | BEFORE THE THERAPY | AFTER 7 DAYS | AFTER 14 DAYS |
|---|---|---|---|
| (3) Intense | 60 patients | 26 patients | 3 patients |
| (2) Middle | 30 patients | 23 patients | 10 patients |
| (1) Light | 15 patients | 45 patients | 10 patients |
| (0) Absent | 0 patients | 5 patients | 77 patients |

The suspension of the application of the gel has been recommended to the patients on the onset of possible side effects which, nevertheless, did not show.

As it results from the Table 3, a net improvement has been obtained in 87 cases, whereas in 10 cases a minimal modification of the initial picture has been noted and in 3 cases, the oncoming of erythema and itching has been observed, yet readily ceased interrupting the application.

Based on the illustrated results, it is possible to observe how the gel showed to possess notable therapeutic effectiveness towards seborrhoeic dermatitis.

Neither thinning of the skin nor hypertrichosis nor teleangectasias have been observed, even after a prolonged use. In the greatest part of the cases, a complete remission occurred, even after the first application.

Example 10

Fifty patients, 35 males and 15 females, between 20 and 60 years old, suffering from scalp seborrhoeic dermatitis, have been treated with the detergent prepared in the composition example No. 2.

The results are illustrated in the following Table 4.

TABLE 4

| SEBORRHEIC DERMATITIS | BEFORE THE THERAPY | AFTER 7 DAYS | AFTER 14 DAYS |
|---|---|---|---|
| (3) Intense | 30 patients | 5 patients | 2 patients |
| (2) Middle | 10 patients | 4 patients | 3 patients |
| (1) Light | 10 patients | 28 patients | 24 patients |
| (0) Absent | 0 patients | 13 patients | 21 patients |

Also in this case, a practically complete (45 patients) remission has been found after two weeks of treatment, in two cases the subsistence of the dermatitis has been found whereas in three cases a light improvement has been obtained.

The invention claimed is:

1. A topical composition comprising:
   a) at least an alum selected among the group consisting of aluminium and an alkaline metal or ammonium double sulfates;
   b) 18-β-glycyrrhetic acid and/or one salt and/or organic or inorganic derivative thereof;
   c) vitamin A and/or one derivative thereof; and
   d) at least a cosmetically acceptable excipient or vehicle.

2. The composition according to claim 1, comprising:
   a) 0.1-97.0% by weight of at least one said alum;
   b) 0.1-1.0% by weight of 18-β-glycyrrhetic acid and/or one salt and/or organic or inorganic derivative thereof;
   c) 0.1-1.0% by weight of vitamin A and/or one derivative thereof, simple and/or hydrogenated and/or a retinoic acid ester or derivatives thereof and/or mixtures obtained by reacting retinol and saccharomycetes polypeptides; and
   d) at least the cosmetically acceptable excipient or vehicle.

3. The composition according to claim 1, comprising:
   a) 0.3-80.0% by weight of at least one said alum;
   b) 0.2-0.8% by weight of 18-β-glycyrrhetic acid and/or one salt and/or organic or inorganic derivative thereof;
   c) 0.15-0.8% by weight of vitamin A and/or one derivative thereof, simple and/or hydrogenated and/or a retinoic acid ester or derivatives thereof and/or mixtures obtained by reacting retinol and saccharomycetes polypeptides; and
   d) at least the cosmetically acceptable excipient or vehicle.

4. The composition according to claim 1, comprising:
   a) 0.5-60.0% by weight of at least one said alum;
   b) 0.3-0.6% by weight of 18-β-glycyrrhetic acid and/or one salt and/or organic or inorganic derivative thereof;

c) 0.3-0.6% by weight of vitamin A and/or one derivative thereof, simple and/or hydrogenated and/or a retinoic acid ester or derivatives thereof and/or mixtures obtained by reacting retinol and saccharomycetes polypeptides; and d) at least the cosmetically acceptable excipient or vehicle.

5. The composition according to claim 1, wherein the alum is potassium undecahydrate alum.

6. The composition according to claim 1, wherein the alum is potassium dodecahydrate alum.

7. The composition according to claim 1, wherein the salt and/or the organic or inorganic derivative of 18-β-glycyrrhetic acid are selected from the group consisting of ammonium 18-β-glycyrrhizzate, potassium and dipotassium 18-β-glycyrrhizzate, disodium and trisodium 18-β-glycyrrhizzate, methyl 18-β-glycyrrhizzate and hydrolyzed 18-β-glycyrrhizzate.

8. The composition according to claim 1, comprising vitamin A or a compound selected from the group consisting of retinyl palmitate, retinyl linoleate and retinoxytrimethylsilane.

9. A method of use comprising topically administering a composition according to claim 1, to skin of a patient for the treatment of inflammatory dermopathies.

10. A method of use comprising topically administering a composition according to claim 1, to skin of a patient for the treatment of cutaneous defects caused by seborrhoeic dermatitis.

11. A method of use comprising topically administering a composition according to claim 1, to skin of a patient for the treatment of cutaneous defects caused by at least one of seborrhoeic dermatitis contact dermatitis, eczemas, and psoriasis.

12. The method according to claim 11, the composition comprising:
a) 0.1-97.0% by weight of at least an alum;
b) 0.1-1.0% by weight of 18-β-glycyrrhetic acid and/or one salt and/or organic or inorganic derivative thereof;
c) 0.1-1.0% by weight of vitamin A and/or one derivative thereof, simple and/or hydrogenated and/or a retinoic acid ester or derivatives thereof and/or mixtures obtained by reacting retinol and saccharomycetes polypeptides; and
d) at least the cosmetically acceptable excipient or vehicle.

13. The method according to claim 11, the composition comprising:
a) 0.3-80.0% by weight of at least an alum;
b) 0.2-0.8% by weight of 18-β-glycyrrhetic acid and/or one salt and/or organic or inorganic derivative thereof;
c) 0.2-0.8% by weight of vitamin A and/or one derivative thereof, simple and/or hydrogenated and/or a retinoic acid ester or derivatives thereof and/or mixtures obtained by reacting retinol and saccharomycetes polypeptides; and
d) at least the cosmetically acceptable excipient or vehicle.

14. The method according to claim 11, the composition comprising:
a) 0.5-60.0% by weight of at least an alum;
b) 0.3-0.6% by weight of 18-β-glycyrrhetic acid and/or one salt and/or organic or inorganic derivative thereof;
c) 0.3-0.6% by weight of vitamin A and/or one derivative thereof, simple and/or hydrogenated and/or a retinoic acid ester or derivatives thereof and/or mixtures obtained by reacting retinol and saccharomycetes polypeptides; and
d) at least the cosmetically acceptable excipient or vehicle.

15. The method according to claim 11, wherein the alum is potassium undecahydrate alum.

16. The method according to claim 11, wherein the alum is potassium dodecahydrate alum.

17. The method according to claim 11, wherein the salt and/or the organic or inorganic derivative of 18-β-glycyrrhetic acid are selected from the group consisting of ammonium 18-β-glycyrrhizzate, potassium and dipotassium 18-β-glycyrrhizzate, disodium and trisodium 18-β-glycyrrhizzate, methyl 18-β-glycyrrhizzate and hydrolyzed 18-β-glycyrrhizzate.

18. The method according to claim 11, the composition comprising vitamin A or a compound selected from the group consisting of retinyl palmitate, retinyl linoleate and retinoxytrimethylsilane.

19. A method of use comprising topically administering a composition according to claim 11, to skin of a patient for the treatment of cutaneous defects caused by seborrhoeic dermatitis.

20. A topical composition consisting of:
a) at least an alum selected among the group consisting of aluminium and an alkaline metal or ammonium double sulfates;
b) 18-β-glycyrrhetic acid and/or one salt and/or organic or inorganic derivative thereof;
c) vitamin A and/or one derivative thereof; and
d) at least a cosmetically acceptable excipient or vehicle selected from at least one member of the group consisting of:

diluents, lactose, dextrose, saccharose, cellulose, lubricating agents, silica, talc, stearic acid, hydrocarbon lubricating agents, glyceride esters, non-glyceride esters, fatty alcohols, cyclic and linear, silicone derivatives, synthetic and natural waxes, paraffins, fatty acids, magnesium stearate, calcium stearate, glycerine, sorbitol, maltitol, monopropylenic glycol, polyethylene glycols; starches, arabic rubbers, gelatin, methylcellulose, carboxymethylcellulose or polyvinylpyrrolidone; dyes;

stearate anionic emulsifying agents, saccharose ester non-ionic emulsifying agents, glucose ester non-ionic emulsifying agents, ethoxylated fatty alcohol non-ionic emulsifying agents, glyceryl monostearate non-ionic emulsifying agents, anionic surfactants, sodium lauryl ethoxy sulfate, sodium lauryl ethoxy citrate, non-ionic surfactants, glucose ester non-ionic surfactants, amphoteric sorbitol esters, cocoamidopropylbetaine, cocoimidazoline, hydroacetates and dehydroacetates, organic aliphatic and aromatic esters, polymers, imidazolidinyl urea, p-oxybenzoates, methylisothiazolinone and methylisothiazolinone chloride, sorbic acid, ethylene diaminotetracetic acid, sweeteners, vegetable extracts, vegetable derivatives, isoflavones, phytosterols, and soy lecithin, inorganic salts, vitamins different from vitamin A and esters thereof, and non-toxic and cosmetically and pharmacologically inactive substances, anti-inflammatory, antimycotic and antimicrobial agents, water, Disodium EDTA, p-methyl hydroxy benzoate, Phenoxy ethanol, Castor oil, Hydroxyethyl cellulose, Monoethanolamine lauryl ethoxy sulfate, Cocodiethanolamide, perfume, EDTA, Sodium chloride, Poliquaternium 10, Triethanolamine, Hydrolysed wheat protein, PEG 8 $C_{12}$-$C_{14}$ alkyl ester, $C_{12}$-$C_{15}$ alkyl benzoate, Cetyl stearyl alcohol, Dimeticone, Cyclomethicone, Hydrogenated lecithin, P-methyl hydroxybenzoate, P-propyl hydroxybenzoate, Polyglyceryl 3-diisostearate, *Ribes nigrum* (Black currant) fruit extract, Polyethylene glycol dipolyhydroxystearate, Tocopheryl acetate, lecithin, tocopherol, ascorbyl palmitate and citric acid, Cyclopentasiloxane, $MgSO_4$, p-hydroxy benzoates, phenoxyethanol, Polymethylmethacrylate, Cetyl stearyl alcohol, Lauryl alcohol, Paraffinum liquidum, Cyclopentasiloxane, Polyglyceril-3 diisostearate, Phenoxyethanol, PEG-30 polyhydroxystearate, Tocopheryl acetate, Oil of *Helianthus annuus* seeds, p-butyl hydroxybenzoate, p-propyl hydroxybenzoate, Lecithin, Tocopherol, Ascorbyl palmitate, Citric acid.

21. The topical composition of claim 20 consisting of:
a) at least an alum selected among the group consisting of aluminium and an alkaline metal or ammonium double sulfates;
b) 18-β-glycyrrhetic acid and/or one salt and/or organic or inorganic derivative thereof;
c) vitamin A and/or one derivative thereof; and
d) at least a cosmetically acceptable excipient or vehicle selected from at least one member of the group consisting of:

diluents, lactose, dextrose, saccharose, cellulose, lubricating agents, silica, talc, stearic acid, hydrocarbon lubricating agents, glyceride esters, non-glyceride esters, fatty alcohols, cyclic and linear, silicone derivatives, synthetic and natural waxes, paraffins, fatty acids, magnesium stearate, calcium stearate, glycerine, sorbitol, maltitol, monopropylenic glycol, polyethylene glycols; starches, arabic rubbers, gelatin, methylcellulose, carboxymethylcellulose or polyvinylpyrrolidone; dyes;

stearate anionic emulsifying agents, saccharose ester non-ionic emulsifying agents, glucose ester non-ionic emulsifying agents, ethoxylated fatty alcohol non-ionic emulsifying agents, glyceryl monostearate non-ionic emulsifying agents, anionic surfactants, sodium lauryl ethoxy sulfate, sodium lauryl ethoxy citrate, non-ionic surfactants, glucose ester non-ionic surfactants, amphoteric sorbitol esters, cocoamidopropylbetaine, cocoimidazoline, hydroacetates and dehydroacetates, organic aliphatic and aromatic esters, polymers, imidazolidinyl urea, p-oxybenzoates, methylisothiazolinone and methylisothiazolinone chloride, sorbic acid, ethylene diaminotetracetic acid, sweeteners, isoflavones, phytosterols, and soy lecithin, inorganic salts, vitamins different from vitamin A and esters thereof, and non-toxic and cosmetically and pharmacologically inactive substances, water, Disodium EDTA, p-methyl hydroxy benzoate, Phenoxy ethanol, Castor oil, Hydroxyethyl cellulose, Monoethanolamine lauryl ethoxy sulfate, Cocodiethanolamide, perfume, EDTA, Sodium chloride, Poliquaternium 10, Triethanolamine, Hydrolysed wheat protein, PEG 8 $C_{12}$-$C_{14}$ alkyl ester, $C_{12}$-$C_{15}$ alkyl benzoate, Cetyl stearyl alcohol, Dimeticone, Cyclomethicone, Hydrogenated lecithin, P-methyl hydroxybenzoate, P-propyl hydroxybenzoate, Polyglyceryl 3-diisostearate, *Ribes nigrum* (Black currant) fruit extract, Polyethylene glycol dipolyhydroxystearate, Tocopheryl acetate, lecithin, tocopherol, ascorbyl palmitate and citric acid, Cyclopentasiloxane, $MgSO_4$, p-hydroxy benzoates, phenoxyethanol, Polymethylmethacrylate, Cetyl stearyl alcohol, Lauryl alcohol, Paraffinum liquidum, Cyclopentasiloxane, Polyglyceril-3 diisostearate, Phenoxyethanol, PEG-30 polyhydroxystearate, Tocopheryl acetate, Oil of *Helianthus annuus* seeds, p-butyl hydroxybenzoate, p-propyl hydroxybenzoate, Lecithin, Tocopherol, Ascorbyl palmitate, Citric acid.

22. A topical composition consisting essentially of:
a) said at least an alum selected among the group consisting of aluminium and an alkaline metal or ammonium double sulfates;
b) said 18-β-glycyrrhetic acid and/or one salt and/or organic or inorganic derivative thereof;
c) said vitamin A and/or one derivative thereof; and
d) said at least a cosmetically acceptable excipient or vehicle.

23. The composition according to claim 22, consisting essentially of:
a) 0.5-60% by weight of at least an alum;
b) 0.2-0.8% by weight of 18-β-glycyrrhetic acid and/or one salt and/or organic or inorganic derivative thereof;
c) 0.15-0.8% by weight of vitamin A and/or one derivative thereof, simple and/or hydrogenated and/or a retinoic acid ester or derivatives thereof and/or mixtures obtained by reacting retinol and saccharomycetes polypeptides; and
d) at least the cosmetically acceptable excipient or vehicle,
wherein the alum is potassium undecahydrate alum or potassium dodecahydrate alum;
wherein the salt and/or the organic or inorganic derivative of 18-β-glycyrrhetic acid are selected from the group consisting of ammonium 18-β-glycyrrhizzate, potassium and dipotassium 18-β-glycyrrhizzate, disodium and trisodium 18-β-glycyrrhizzate, methyl 18-β-glycyrrhizzate and hydrolyzed 18-β-glycyrrhizzate,
wherein the vitamin A and/or one derivative thereof is selected from the group consisting of vitamin A or a compound selected from the group consisting of retinyl palmitate, retinyl linoleate and retinoxytrimethylsilane.

* * * * *